(12) United States Patent
Rathi

(10) Patent No.: US 8,758,277 B2
(45) Date of Patent: Jun. 24, 2014

(54) NEUROMUSCULAR TESTING DEVICE AND METHOD TO USE

(71) Applicant: Prachi Rathi, Jacksonville, FL (US)

(72) Inventor: Prachi Rathi, Jacksonville, FL (US)

( * ) Notice: Subject to any disclaimer, the term of this patent is extended or adjusted under 35 U.S.C. 154(b) by 0 days.

(21) Appl. No.: 13/957,847

(22) Filed: Aug. 2, 2013

(65) Prior Publication Data

US 2013/0338542 A1     Dec. 19, 2013

Related U.S. Application Data

(63) Continuation of application No. 13/483,178, filed on May 30, 2012.

(51) Int. Cl.
*A61B 5/103* (2006.01)
*A61B 5/11* (2006.01)
*A61B 5/107* (2006.01)

(52) U.S. Cl.
CPC .................. *A61B 5/11* (2013.01); *A61B 5/1072* (2013.01); *A61B 5/1124* (2013.01)
USPC ............................ 600/595; 600/587; 482/138

(58) Field of Classification Search
CPC .... A61B 5/4528; A61B 5/103; A61B 5/0053; A61B 5/1071
USPC .............. 482/15, 23, 33, 105, 138, 148, 910; 600/587, 595; 601/33
See application file for complete search history.

(56) References Cited

U.S. PATENT DOCUMENTS

| | | | | |
|---|---|---|---|---|
| 4,208,050 A | * | 6/1980 | Perrine et al. | 482/148 |
| 4,323,234 A | * | 4/1982 | Glaese | 482/148 |
| 4,895,543 A | * | 1/1990 | Vermette | 482/148 |
| 5,031,903 A | * | 7/1991 | Clarke | 482/148 |
| 5,470,037 A | * | 11/1995 | Willis | 248/125.9 |
| 5,586,558 A | * | 12/1996 | Riley | 600/594 |
| 2010/0120587 A1 | * | 5/2010 | Alexander et al. | 482/52 |

* cited by examiner

*Primary Examiner* — Sean Dougherty
*Assistant Examiner* — Daniel Cerioni
(74) *Attorney, Agent, or Firm* — Lawrence J. Gibney, Jr.

(57) ABSTRACT

Health care professionals must often measure a person's neuromuscular function. Currently there is no way to accurately assess the level of a person's ability to perform basic tasks that will permit the person to perform the activities of daily activity and thus determine whether or not the person can be discharged from the hospital or whether additional assistance may be needed. This device will allow the health care professional to accurately assess these functions so that decisions regarding discharge from a health care facility or return to home may be made.

7 Claims, 7 Drawing Sheets

NEUROMUSCULAR TESTING DEVICE AND METHOD TO USE

This is a continuation in part of a previously filed application with Ser. No. 13/483,178 and a filing date of May 30, 2012. The undersigned in claiming the priority filing date based on the earlier filed application.

BACKGROUND OF THE INVENTION

A. Field of the Invention

This relates to the field of rehabilitation and specifically a way to measure the neuromuscular function of a patient with the use of one device. Neuromuscular damage can occur as a result of stroke, head injury, or any other diseases or conditions that affect the brain or muscles.

Neuromuscular functioning controls our ability to speak, touch, feel, see, and hear in addition to allowing us to balance and walk. Individuals who have suffered any type of brain trauma or physical disability from whatever cause are likely to suffer some damage to their neuromuscular functioning.

The ability to specifically quantify during assessment and later the progress of a patient will impact decisions on whether the patient is able to be discharged alone or whether the person should have some assistance when the person returns to his or her home. In some cases, this type of measurement may also determine whether or not the person should be sent to a separate rehabilitation facility for additional therapy and services.

B. Prior Art

There are many prior art references to rehabilitation devices. Many of the devices in the prior art teach ways to measure specific physical function such as the ability to push or pull an object.

Representative examples in the prior art include King U.S. Pat. No. 5,484,355 Michel U.S. Pat. No. 5,632,052 and Hall U.S. Pat. No. 5,839,991.

The device in Hall possesses some similar features but does not include all the features that are provided or taught with the current device.

The current device is a device that will allow the health care professional a means to specifically quantify a person's neuromuscular functioning in terms of their specific ability to reach in all planes as well as test their ability to control eye movements, among other attributes. The advantage of the current device is that the device will be able to quantify identifiable measurements in order to precisely determine the progress of a patient's recovery. The device will take the guesswork out of these measurements and will avoid the problem of attempting to discern the readings from another therapist.

The current device will also enable a person to measure movement in all directions and planes; this type of measurement is important to determine whether or not the person is ready or able to return home with or without assistance.

BRIEF SUMMARY OF THE INVENTION

One of the challenges for therapists is to be able to quantify the patient's abilities during initial assessment and subsequent improvement in the patient from an objective standard. This device will allow a therapist to measure both linear and angular measurements so that an objective measurement of the patient's progress can be recorded.

This is a device that is designed to be portable and can be moved with one hand. A pole will rest on a base with a protractor onto which a plurality of wheels are placed so that the entire device can be moved easily. The wheels will be lockable so that the device can be placed in one position, when needed.

The center pole can telescope so that the device can be placed at the ideal height for the individual. Ideally the nut which affixes the arms to the pole will be aligned with the person's sternum if the person is facing the device and at the acroniom process of the person if the device is sideways with respect to the patient.

This device will be helpful to measure a multitude of ranges of motions for the body parts including the shoulder, back and neck. It will allow the therapist to measure functional shoulder flexion, trunk flexion, trunk flexion with rotation, abduction and adduction of limbs in addition to other body movements.

On the top of the pole will be a plurality of arms that rotate around a pin that is specifically designed to be moved by a single person and called a tripod nut. On each of the arms will be a series of markings that will measure the distance from a given point so that the therapist can measure the distance that the patient can move an object or touch an object. The arms can be locked in place and are color coded.

Because some individuals may have other physical impairments including impaired vision or hearing, the arms may also be illuminated or be equipped with an audible signal.

On each arm will be a window that will allow the therapist to read the degrees that are marked on the protractor that is attached to the pole. On the central end of each arm will be a cutout portion or window so that the therapist can easily view the protractor that is located behind the arm. This will permit the therapist to specifically measure the angle of the arm so that a precise measurement can be obtained.

It is contemplated that there will be eight arms used on this device and each of the arms will operate independently of each other and all can lock in place.

The arms are of sufficient length so that the device will test the reach of the individual including diagonal reach. Because of the gradations on each of the arms, the therapist will be able to specifically determine the "amount of reach" of the person. Each therapist who interacts with the person can then easily perform follow up exercises and measurements.

These arms will be on both sides of the device and all parts all rotate around the pin. The system is fastened with a tripod nut.

Before a patient should be discharged from a facility such as a hospital or nursing facility, a range of the ability of the person must be carefully measured in order to insure that the transition to another environment is beneficial for the patient as well as safe for the patient.

Some of the skills that are addressed include eye movement exercise and rehabilitation for vertigo and vestibular system analysis, neck movements, eye-hand coordination, gross and fine motor coordination, visual-motor skills retraining, visual-perceptual skills, dexterity skills retraining, and cognitive skills retraining are just some of the areas that should be tested. These are a representative listing of functions to be tested and are not an exhaustive list.

On the sides of the pole will be a plurality of baskets that can telescope outward so that the person's ability to reach below the waist is tested. The baskets will be attached to the pole with a bushing that can be locked in place. Again all the features of this device are carefully designed to test the various areas that need to be evaluated.

Another skill that is critical is the ability to reach at an angle. This simulates a person who needs to reach at an angle to place something in a cabinet or the refrigerator. With this device the person typically stands in front of the device and the therapist asks the patient to perform certain tasks. The therapist will also ask the person to perform certain maneuvers from side to side at different angles.

To measure the ability of a person to move from side to side a base protractor is affixed to the base. A pointer is also placed on the top surface of the base protractor. The pointer allows the device to be moved at an angle relative to the person to measure the ability to reach at an angle. With the protractor the therapist can make detailed, specific measurements as to the person's ability to reach from side to side.

The device also has the ability to expand and incorporate other games and activities to test specific functions as the therapist modifies the activity.

NUMBERING DESCRIPTION

Figure 1:
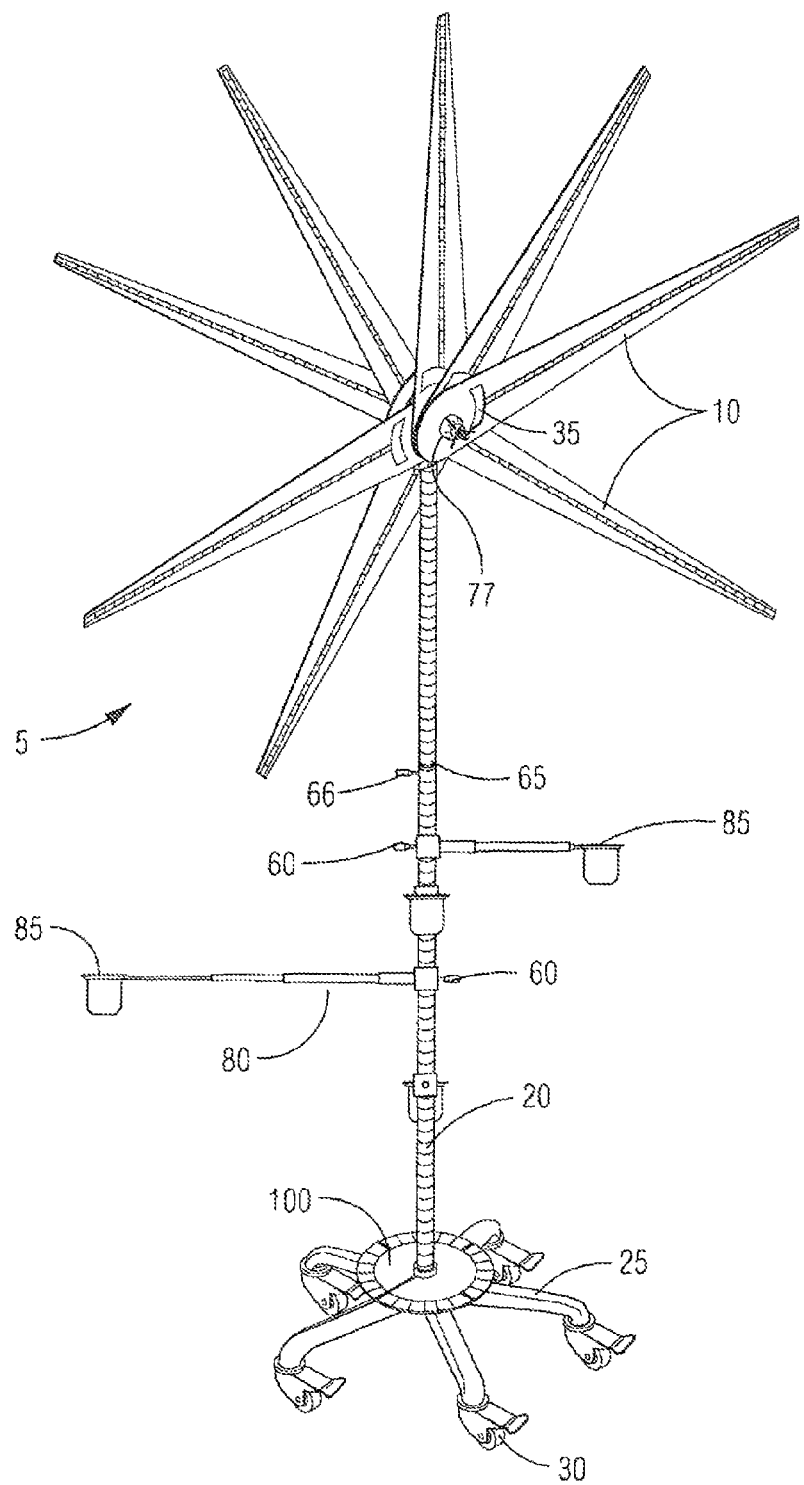
FIG. 1 is an isometric view of the device.
Figures 2, 2A:
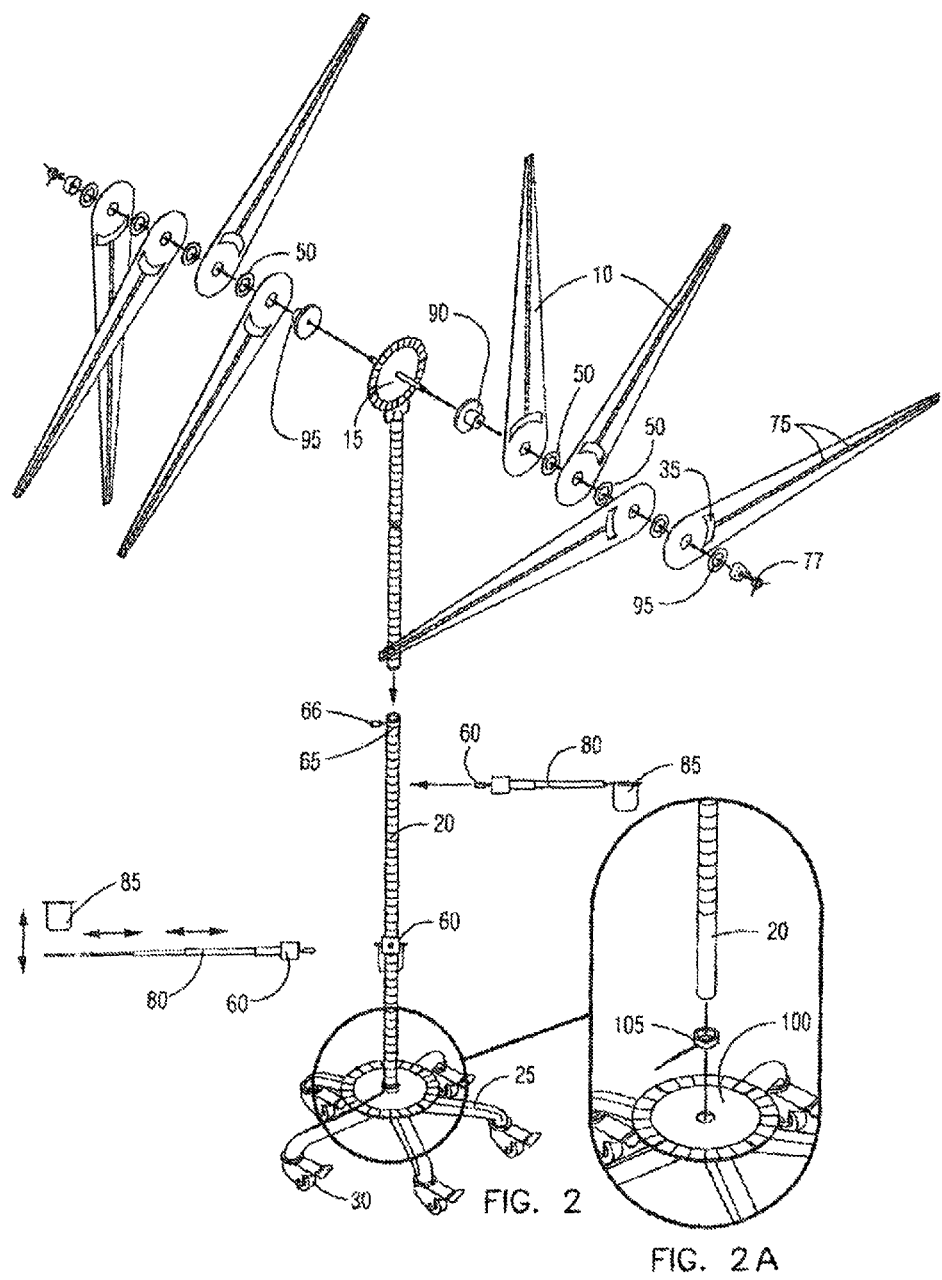
FIG. 2 is an exploded isometric view of the device with the retractable buckets and the arms separated from the stand.
FIG. 2A is a exploded view of the stand depicting the base protractor and pointer.
Figure 3:
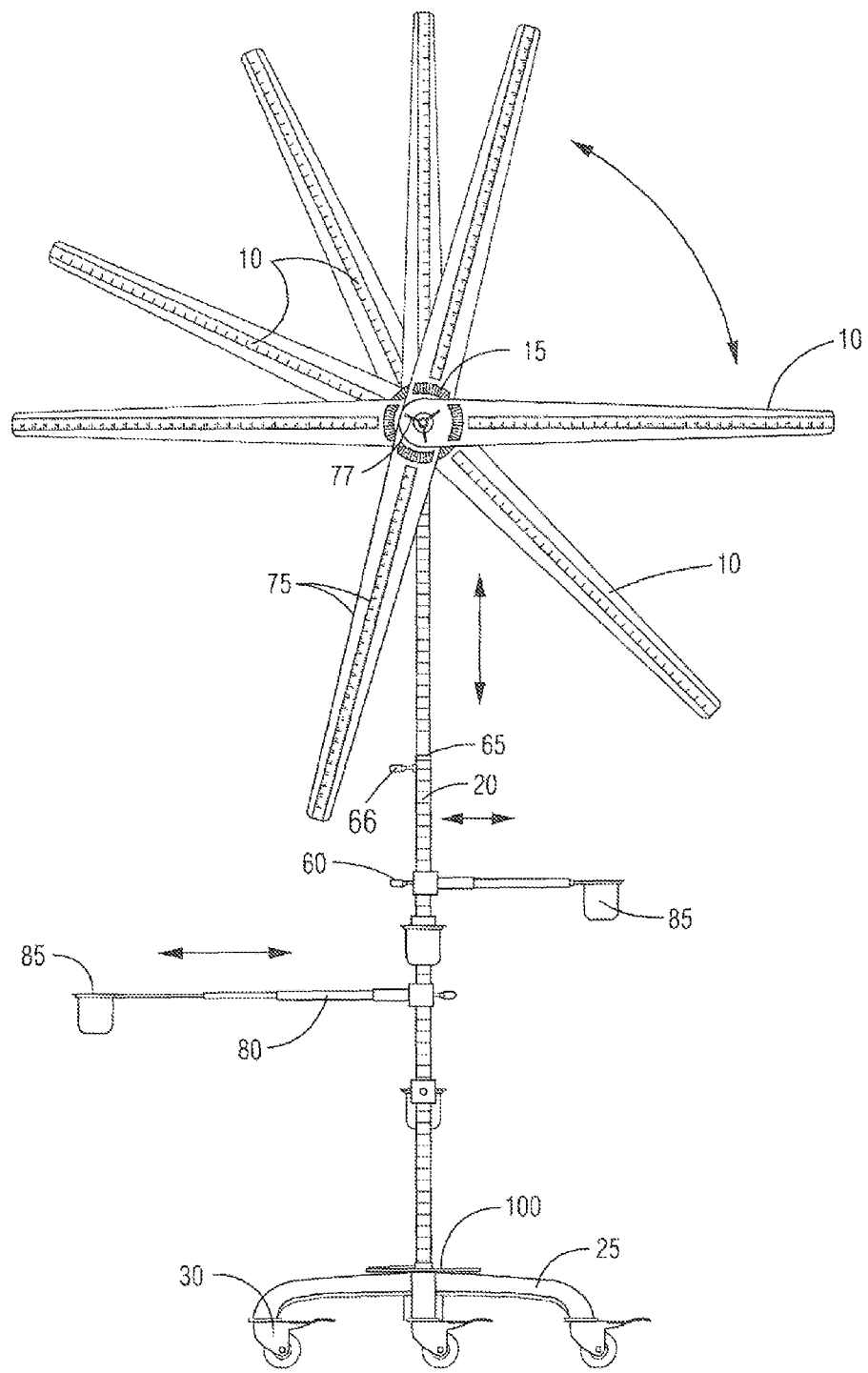
FIG. 3 is a front view of the device.
Figure 4:
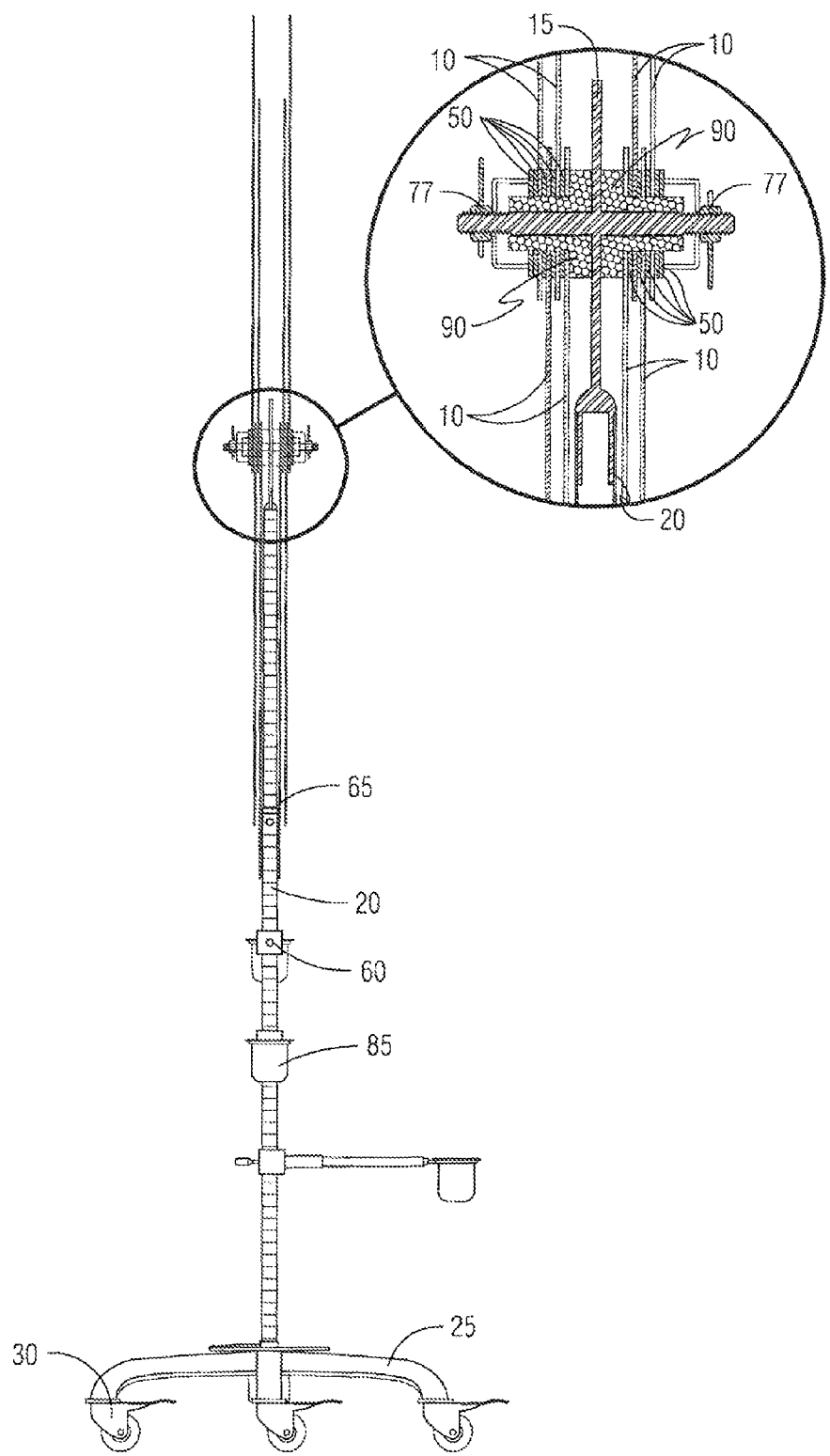
FIG. 4 is a side view of the device with an enlarged view of the connection means for the arms.
Figure 5:
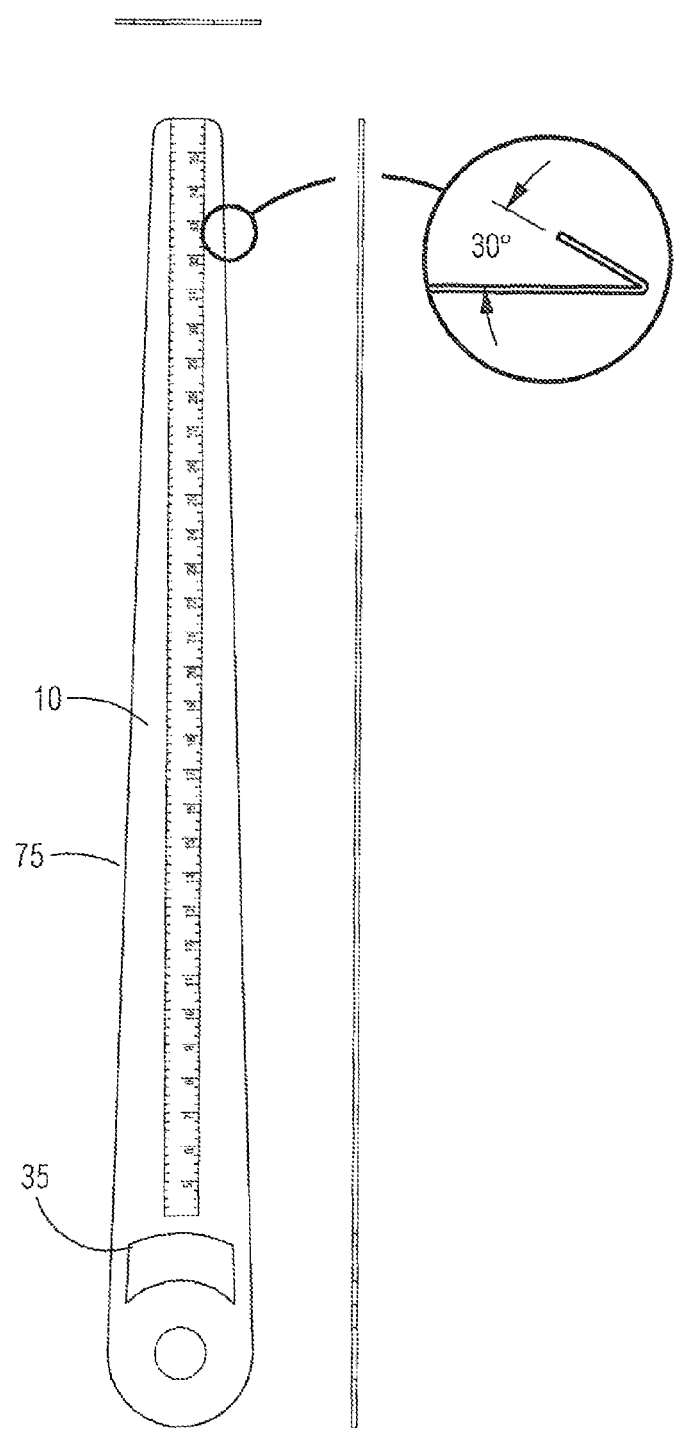
FIG. 5 is a front view of the arm with the window depicted at the end of the arm.
Figure 6:
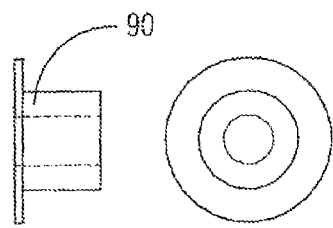
FIG. 6 is a side view of the bushing.
Figure 7:
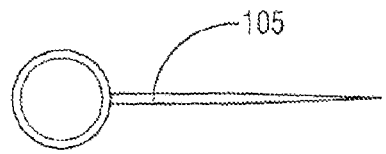
FIG. 7 is a top view of the protractor pointer.
Figure 8:
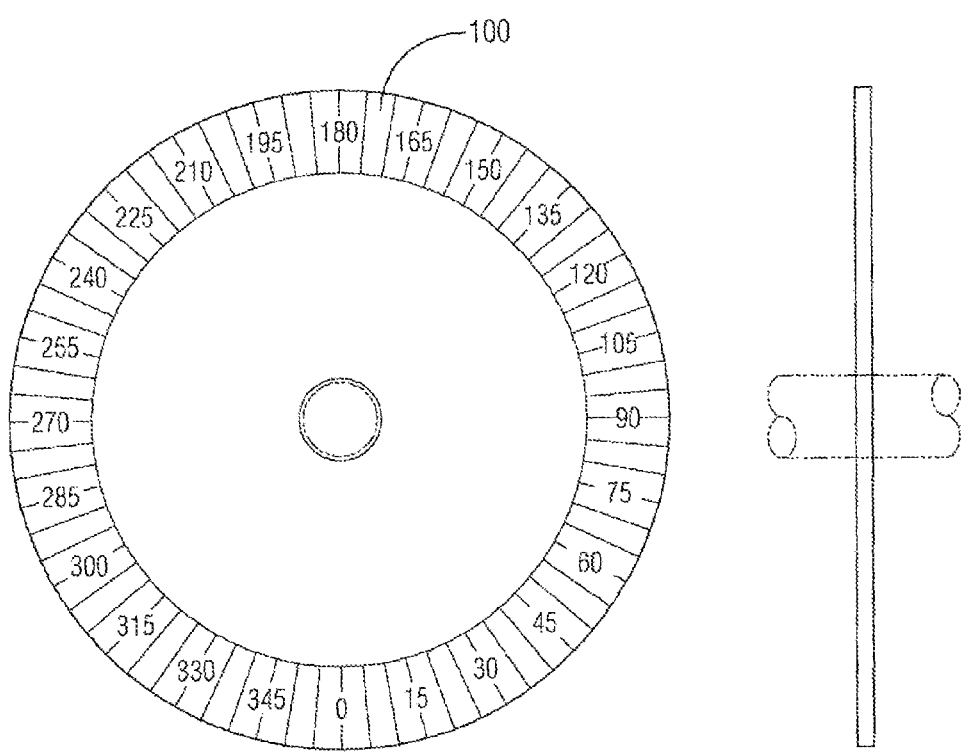
FIG. 8 is top view of the base protractor.
Figure 9:
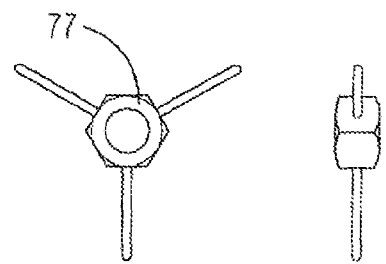
FIG. 9 is a front view of the tripod nut.
Figure 10:
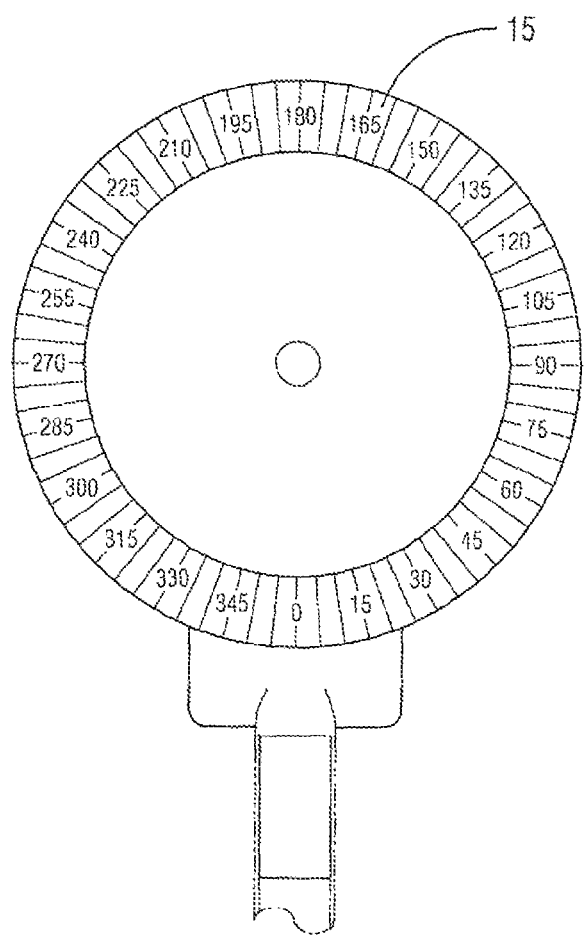
FIG. 10 is a front view of the protractor.

5—Device
10—Arm
15—Protractor
20—First pole
25—Base
30—Wheels
35—Window and arm
40—Pin
50—Washer
55—First end of stand
60—Attachment means for basket
65—Second pole
66—Locking Means for Stand
70—Degree markings on protractor
75—Gradient markings on arm
77—Tripod Nut
80—Basket Arm
85—Basket
90—First Bushing
95—Second Bushing
100—Base protractor
105—Base protractor pointer

DETAILED DESCRIPTION OF THE EMBODIMENTS

This is a device that will enable the health care professional to accurately assess the neuromuscular functioning of a patient. It is designed to be portable and rests on a plurality of wheels. The stand is designed to telescope.

The rehabilitation device 5 will rest on a base 25 and is comprised of a straight first pole 20 that is secured to the base 25. The base 25 will have wheels 30 that will be lockable so the device can be moved into a position and then be locked in place. The base will secure the first pole 20. A second pole 65 will be inserted into a portion of the first pole 20, which is partially hollow. The height of the first pole 20 can be adjusted so that the height of different individuals can be accommodated with this device; the two pole sections are connected together using a means of connection 66, which may be a set screw although other types of connection means may be used. Ideally the tripod nut 77 that secures the arms 10 will align with the person's sternum and appropriate adjustment of the second pole section 65 is made by the therapist.

On the bottom portion of the stand 25 will be a plurality of attachment means for baskets 60 to again accommodate the different heights of individuals when testing for neuromuscular function from side to side or forward bend to reach below the waist.

A basket 85 that can telescope outward and away from the stand will be used to test the range of motion of a person bending forward and outward as well as sideways and backward below the waist. It is contemplated that there will be four baskets attached to the first pole section 20. Each of the baskets will be attached to telescoping arms 80 so that the therapist can adjust the length of the basket away from the stand 20.

On one first end of the second pole section 65 will be a member that has an opening through which a pin 40 will be inserted. On the pin will be two bushings 90,95 and washers 50 to secure the arms 10 and a protractor 15. It is contemplated that a specially designed tripod nut 77 will be used to secure the arms and protractor 15 in place. The tripod nut 77 can be moved easily be the therapist.

The protractor 15 that has three hundred and sixty degrees represented on it will be placed behind a plurality of arms 10.

It is contemplated that there will be eight arms 10 to cover the significant directions on a compass (north, northeast, east southeast, south, southwest, west and northwest), and each arm 10 will be three to four feet in length for a total of six to eight feet across to insure that all heights of individuals or lengths of arms may be tested.

On each of the arms 10, markings 75 will be calibrated like a ruler so that the therapist can easily quantify the distance away from a central point that the person's reach in any given direction can be accurately measured.

A window 35 will appear on the proximal end of the arm 10 so that the therapist can read the degrees on the protractor 15 that is located behind the arm 10 at a given angle position. There will be a plurality of degree marks on the protractor 15 so the therapist can easily quantify the degree at which the arm 10 is positioned. The position of the arms 10 as well as the length that the person can reach along an arm are measurements that a therapist will use in his or her determination about the progress of a person's abilities.

The arms 10 can all be locked in place using the tripod nut 77 and all the arms are designed to work independently of each other. A first and second bushing 90, 95 secures the plurality of arms to one end of the second straight pole on both sides of the second straight pole and permits rotation of the plurality of arms.

Because some persons may have vision or hearing problems there may be a means to illuminate the arms or emit an audible sound for the person who is being tested. Additionally it may be easier for an individual to place objects on the arm so the use of magnetic objects to be placed on the metallic arms is also contemplated.

Additionally the arms 10 will be color coded so that the health care professional can accurately test the proper movement of a person's eyes. For instance, the health care professional may ask the patient to move his or her eyes from the red arm to the green arm, after they have been placed in the appropriate position and observe the movement of the eyes. This type of movement will enable the therapist to evaluate the person's eye functions as well as the cognitive functions.

Around the protractor 15, there will be degree markings 70 on the protractor, which has three hundred and sixty degrees so the therapist can easily quantify the specific angle at which the arm 10 is positioned. On each of the arms will be a clear opening 35 at one end of the arm 10 to enable the therapist to read the degree of angle at which the arm is positioned.

The purpose of the device is for a therapist to measure the physical progress for a patient who is suffering from neuromuscular dysfunction and can easily quantify the degree of improvement and highlight areas of improvement that may be needed. The data that can be measured is done in such a way so that the data can easily be read from therapist to therapist as the patient continues with his or her recovery.

During use the therapist would place the device in a given position and arrange the position of the arms according to the prescribed area of neuromuscular functioning to be tested. This may involve the position of the arms as well as the position of the baskets.

The patient is placed in front of the device and the tripod nut 77 is positioned at about the level of the sternum of the person when the person is facing the device or at the acroniom process of the patient if the patient is positioned sideways with respect to the device. The therapist then instructs the patient to move in certain directions such as reaching in certain directions. As the person moves in a given direction the person may touch one of the arms and the measurements are recorded. The therapist customizes the commands to the patient depending on the specific issue to be addressed by the therapist and suggested therapy.

A base protractor 100 will be affixed to the top of a base plate. On the top surface of the base protractor 100 will be a base protractor pointer 105 that can rotate over the top surface of the base protractor 100. The therapist can place the base protractor pointer 105 on a designated angle relative to the person and move the device so that the person's ability to reach at an angle can be objectively measured. This type of movement is critical to determine whether or not the person can reach to place items in a cabinet or in a refrigerator, typically by reaching at an angle as well reaching directly in front of the person. With the base protractor pointer the therapist can move the device to a multitude of positions relative to the patient and measure the displacement with respect to the patient.

As the patient is performing the different physical activities, the therapist is recording the physical measurements according to the gradations on the arms and the angle that is read on the protractor for or during exercises. The patient may similarly be asked to perform physical maneuvers such as placing items in or out of the basket(s) that have been extended away from the stand. Similarly the therapist records the distance away from the stand that the person can place and/or retrieve objects.

Ideally the therapist charts the data so that the next therapist who interacts with the patient can determine quickly the progress that a patient has made.

When not in use, the arms 10 can be locked and stored in vertical alignment.

While the embodiments of the invention have been disclosed, certain modifications may be made by those skilled in the art to modify the invention without departing from the spirit of the invention.

The inventor claims:

1. A neuromuscular testing device which is comprised of:
a. a stand;
wherein the stand is of a predetermined size;
wherein a plurality of wheels are placed on bottom of the stand;
wherein a base plate is placed on the stand;
b. a first pole;
wherein the first pole is secured to the stand;
wherein the first pole can be locked in place;
said first pole can telescope;
wherein one end of the first pole is hollow;
c. a second straight pole;
wherein a portion of the second straight pole is inserted into the end of the first pole;
wherein a means of connection is provided to pole;
wherein an opening is provided on the first end of the second straight pole;
wherein a pin passes through the center of the opening;
said pin supports a plurality of bushings;
said pin supports a plurality of washers;
d. a protractor;
wherein the protractor is attached to the second pole;
wherein the protractor has markings for angle measurements;
said protractor having markings for three hundred and sixty degrees;
e. a plurality of arms;
wherein the plurality of arms is of a predetermined length;
wherein a series of markings are placed on the plurality of arms;
said markings indicate the distance from the opening on the first end;
wherein the first pole and the second pole have a first axis extending from the first end of the first pole to the second end of the second pole;
wherein the plurality of arms are configured to rotate about a second axis;
the second axis being perpendicular to the first axis;
wherein the plurality of arms operate independently of each other;
wherein the plurality of arms is color coded;
f. a window;
wherein the window is provided on one end of each of the arms;
wherein the window is placed over the protractor;
said window permits a therapist to record measurements;
g. a plurality of baskets;
wherein the plurality of baskets is attached to the pole;
said baskets extend horizontally away from the pole;
said baskets can be removed from the pole;
wherein a means to attach the baskets to the pole is provided;
h. a means to lock the plurality of arms;
wherein the means to lock the plurality of arms is provided;
i. a base protractor;
wherein the base protractor is affixed to the base;
said protractor has markings for three hundred and sixty degrees;
j. a base protractor pointer;
wherein the base protractor pointer is free to rotate over a top surface of the base protractor.

2. The device as described in claim 1 wherein a means to illuminate the plurality of arms is provided.

3. The device as described in claim 1 wherein a means to emit an audible sound is provided on the plurality of arms.

4. The device as described in claim 1 wherein a magnetic item is placed on a metallic arm.

5. The device as described in claim 1 wherein the means to lock the plurality of arms is a tripod nut.

6. The device as described in claim 1 wherein the plurality of arms are different colors for instructional purposes.

7. A method to use the device of claim 1, the method comprising the following steps:
   a. placing the device at a given position;
   b. positioning each of the plurality of arms in a predetermined configuration;
   c. positioning the baskets in a predetermined configuration;
   d. placing the device at an angle relative to the patient;
   e. asking the patient to perform certain physical activities;
   f. recording a measurement of the stand relative to the patient using the base protractor;
   g. recording the data obtained from physical activities of functional reaching in multiple directions and planes from the arms.

* * * * *